US011299444B2

(12) United States Patent
Sattler et al.

(10) Patent No.: US 11,299,444 B2
(45) Date of Patent: Apr. 12, 2022

(54) SELECTIVE HYDROGEN REMOVAL (71) Applicant: ExxonMobil Research and Engineering Company, Annandale, NJ (US)

(72) Inventors: Aaron Sattler, Annandale, NJ (US); Michele L. Paccagnini, Randolph, NJ (US); Pedro M. Serna Merino, Branchburg, NJ (US); Henry K. Klutse, Hillside, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 57 days.

(21) Appl. No.: 17/084,748

(22) Filed: Oct. 30, 2020

(65) Prior Publication Data
US 2021/0155565 A1    May 27, 2021

Related U.S. Application Data (60) Provisional application No. 62/939,939, filed on Nov. 25, 2019.

(51) Int. Cl.
*C07C 5/48*    (2006.01)
*B01J 29/74*    (2006.01)

(52) U.S. Cl.
CPC .............. *C07C 5/48* (2013.01); *B01J 29/743* (2013.01); *C07C 2529/74* (2013.01)

(58) Field of Classification Search
CPC ......... C07C 5/48; C07C 11/02; C07C 5/3337; C07C 11/22; C07C 2522/42;
(Continued)

(56) References Cited

U.S. PATENT DOCUMENTS 4,788,371 A    11/1988 Imai
6,103,103 A *    8/2000 Alexander ............ C07C 5/3337
                                                    208/138
(Continued)

FOREIGN PATENT DOCUMENTS

EP    0219271 A1    4/1987
EP    0219272 A1    4/1987

OTHER PUBLICATIONS

Moliner, Manuel, et. al., Reversible Transformation of Pt Nanoparticles into Single Atoms inside High-Silica Chabazite Zeolite J. Am. Chem. Soc. 2016, 138, pp. 15743-15750.
(Continued)

*Primary Examiner* — Sharon Pregler
(74) *Attorney, Agent, or Firm* — Robert A. Migliorini (57) ABSTRACT

Processes are provided for the removal of hydrogen from a mixture. The process can be performed by contacting a mixture comprising hydrogen, oxygen, and one or more organic compounds with a synthetic zeolite to produce water or steam. The synthetic zeolite can include Si and Al and has a $SiO_2:Al_2O_3$ molar ratio of greater than 4:1, an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI, a degree of crystallinity of at least 80% as measured by ASTM D535-197, and at least 0.01 wt % of at least one catalytic metal, based on a weight of the synthetic zeolite, where the at least one catalytic metal can include Ru, Rh, Pd, Ag, Os, Ir, Pt, Au, Mo, W, Re, Co, Ni, Zn, Cr, Mn, Ce, Ga, alloys thereof, or mixtures thereof. At least 95% of the catalytic metal can be disposed within a plurality of pores of the synthetic zeolite.

25 Claims, 2 Drawing Sheets

(58) Field of Classification Search
CPC ... C07C 2523/44; C07C 2529/74; C07C 1/20; C07C 2521/06; C07C 2521/08; C07C 2523/04; C07C 2523/06; C07C 2523/40; C07C 2523/52; C07C 2523/56; C07C 2523/60; C07C 2529/86; B01D 2255/1021; B01D 2255/1023; B01D 2255/106; B01D 2255/50; B01D 2255/9205; B01D 53/8628; B01D 53/94; B01J 23/42; B01J 23/44; B01J 23/52; B01J 23/58; B01J 23/60; B01J 23/62; B01J 29/62; B01J 29/74; B01J 29/86; B01J 37/04; B01J 37/10; B01J 37/14; B01J 37/18

See application file for complete search history.

(56) References Cited

U.S. PATENT DOCUMENTS 10,512,904 B2 * 12/2019 Otto .................. B01J 35/0013
2019/0168197 A1 6/2019 Canos et al.

OTHER PUBLICATIONS

Moliner, Manuel, et. al., Trapping of Metal Atoms and Metal Clusters by Chabazite under Severe Redox Stress ACS Catal. 2018, 8, pp. 9520-9528.

* cited by examiner

SELECTIVE HYDROGEN REMOVAL

FIELD

Embodiments disclosed herein relate to processes for the removal of hydrogen from a mixture that includes hydrogen and one or more organic compounds. More particularly, such embodiments relate to processes for the dehydrogenation of organic compounds that involves the removal of hydrogen obtained by dehydrogenating the organic compounds.

BACKGROUND

The removal of hydrogen from a mixture of hydrogen and one or more organic compounds is often desirable, for example in a process for the dehydrogenation of organic compounds. In the dehydrogenation of organic compounds, the reaction quotient between dehydrogenatable organic compounds and dehydrogenated organic compounds is influenced by the amount of hydrogen present, as limited by thermodynamic equilibrium. To shift the reaction quotient toward the production of the dehydrogenated organic compounds, hydrogen can be removed from a mixture of hydrogen, dehydrogenatable organic compounds, and dehydrogenated organic compounds.

Many different techniques are known for the removal of a compound from a mixture of that substance with other compounds. Examples of such techniques include crystallization, distillation, liquefaction, solvent extraction, absorption, membrane separation, and chemical reaction. In practice, however, it is difficult to remove hydrogen from a mixture of hydrogen and one or more organic compounds, especially from a mixture of dehydrogenatable and dehydrogenated organic compounds.

Numerous processes have been disclosed that involve the removal of hydrogen from a mixture of hydrogen and one or more organic compounds. For example, U.S. Pat. No. 4,788,371, discloses a process for the dehydrogenation of hydrocarbons in which hydrogen obtained by the dehydrogenation of the hydrocarbons is chemically reacted with oxygen gas in the presence of a catalyst. A disadvantage of all of these processes is that some of the oxygen gas reacts with the organic compounds instead of hydrogen, thus converting them into undesired products, like carbon dioxide or carbon monoxide.

European Pat. Nos.: A1-0219271 and A1-0219272 also disclose processes for the dehydrogenation of hydrocarbons in which hydrogen obtained by the dehydrogenation of the hydrocarbons is removed. Dehydrogenation takes place in the presence of a zeolite catalyst and the hydrogen is removed by chemical reaction with an acidic oxide gas such as sulfur dioxide or nitrous oxide. Sulfur dioxide and nitrous oxide are not as reactive as oxygen toward the organic compounds. This process, however, does not effectively remove hydrogen.

There is a need, therefore, for improved processes to remove hydrogen from a mixture that includes hydrogen and one or more organic compounds.

SUMMARY

In one aspect, a process for the removal of hydrogen from a mixture is provided. The process can include contacting a mixture including hydrogen, oxygen, and one or more organic compounds with a synthetic zeolite to produce water or steam. The synthetic zeolite can include Si and Al and have a $SiO_2:Al_2O_3$ molar ratio of greater than 4:1. The synthetic zeolite can include an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI. The synthetic zeolite can have a degree of crystallinity of at least 80%. The synthetic zeolite can include at least 0.01 wt % of at least one catalytic metal, based on a weight of the synthetic zeolite, where the catalytic metal can include Ru, Rh, Pd, Ag, Os, Ir, Pt, Au, Mo, W, Re, Co, Ni, Zn, Cr, Mn, Ce, Ga, alloys thereof, or mixtures. At least 95% of the catalytic metal can be disposed within the plurality of pores of the synthetic zeolite.

In another aspect, the process can include contacting a mixture including hydrogen, oxygen, and one or more organic compounds with a synthetic zeolite, where at least 80% of the one or more organic compounds are branched or cyclic hydrocarbons. The synthetic zeolite can include a degree of crystallinity of at least 80%, an 8-membered ring zeolite having a framework type of CHA, and at least 0.01 wt % of at least one catalytic metal, based on a weight of the synthetic zeolite, where the at least one catalytic metal comprises Ru, Rh, Pd, Ag, Os, Ir, Pt, Au, Mo, W, Re, Co, Ni, Zn, Cr, Mn, Ce, Ga, alloys thereof, or mixtures thereof. At least 95% of the catalytic metal can be disposed within a plurality of pores of the synthetic zeolite.

In another aspect, the process can include contacting one or more dehydrogenatable organic compounds with a first dehydrogenation catalyst in a first reactor to produce a first mixture of hydrogen, dehydrogenatable organic compounds, and dehydrogenated organic compounds. The mixture of hydrogen, dehydrogenatable organic compounds, and dehydrogenated organic compounds can be contacted with a synthetic zeolite in a second reactor to produce a second mixture comprising a reduced amount of hydrogen. The synthetic zeolite can include, Si and Al and has a $SiO_2:Al_2O_3$ molar ratio of greater than 4:1, a degree of crystallinity of at least 80% as measured by ASTM D535-197, an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI; and at least 0.01 wt % of at least one catalytic metal, based on a weight of the synthetic zeolite, where the at least one catalytic metal can include Ru, Rh, Pd, Ag, Os, Ir, Pt, Au, Mo, W, Re, Co, Ni, Zn, Cr, Mn, Ce, Ga, alloys thereof, or mixtures thereof. At least 95% of the catalytic metal can be disposed within a plurality of pores of the synthetic zeolite. The second mixture can be contacted with a second dehydrogenation catalyst in a third reactor to produce a third mixture including an increased amount of the dehydrogenated organic compounds.

In another aspect, the process can include contacting a mixture including hydrogen, oxygen, and one or more organic compounds with a synthetic zeolite at a temperature of less than 250° C. to produce water or steam. The synthetic zeolite can include, an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI, a degree of crystallinity of at least 80% as measured by ASTM D535-197, and at least 0.01 wt % of at least one catalytic metal, based on a weight of the synthetic zeolite, where the at least one catalytic metal can include Ru, Rh, Pd, Ag, Os, Ir, Pt, Au, Mo, W, Re, Co, Ni, Zn, Cr, Mn, Ce, Ga, alloys thereof, or mixtures thereof.

At least 95% of the catalytic metal can be disposed within a plurality of pores of the synthetic zeolite.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

It is to be understood that the following disclosure describes several exemplary embodiments for implementing different features, structures, and/or functions of the invention. Exemplary embodiments of components, arrangements, and configurations are described below to simplify the present disclosure; however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. Moreover, the exemplary embodiments presented below can be combined in any combination of ways, i.e., any element from one exemplary embodiment can be used in any other exemplary embodiment, without departing from the scope of the disclosure.

The term "hydrogen", as used herein, refers to molecular hydrogen or $H_2$.

The term "largest dimension", as used herein, when discussing particle size means the largest dimension as measured by TEM. In the case of substantially spherical particles, the largest dimension of a particle will correspond to its diameter.

The term "oxygen", as used herein, refers to molecular oxygen or $O_2$.

The term "percentage of the particles by number", as used herein, refers to the arithmetic average of the number of particles having the required characteristic out of 100 particles, this value being determined on the basis of a population of at least one thousand particles.

The term "selective hydrogen combustion" shall mean reacting hydrogen with oxygen to form water or steam without substantially reacting other organic compounds with oxygen to form carbon monoxide, carbon dioxide, and/or oxygenated hydrocarbons.

The term "small pore size zeolite" as used herein, refers to a zeolite having a pore size of about 0.3 nm to 0.5 nm. The small pore size zeolite can have an 8-membered ring framework structure but some 9- or 10-membered ring zeolites are known to have distorted rings which have a size of 0.3 nm to 0.5 nm and fall within the scope of the term "small pore size zeolite". A number of 8-membered ring zeolites are listed in the "Atlas of Zeolite Framework Types", eds, Ch. Baerlocher, L. B. McCusker, D. H. Olson, Elsevier, Sixth Revised Edition, 2007.

The term "synthetic zeolite" should be understood to refer to a zeolite prepared from a synthesis mixture as opposed to a naturally occurring zeolite obtained by mining or quarrying or similar processes from the natural environment.

It has been surprisingly and unexpectedly discovered that small pore zeolites that contain a catalytic metal inside the pores of the zeolite can selectively combust hydrogen from a mixture of hydrogen and other organic compounds at temperatures less than 250° C. Hydrogen and oxygen can flow into the pores of zeolite, while larger organic compounds will not fit inside the pores. The hydrogen and oxygen can contact the catalytic metal that is inside the pores and selectively combust to form water or steam. However, the larger organic compounds that did not fit into the pores do not contact the catalytic metal and do not react with either the hydrogen or the oxygen present.

Hydrogen Removal

In some examples, hydrogen can be removed from a mixture of hydrogen, oxygen, and one or more organic compounds by selective hydrogen combustion using a small pore zeolite containing catalytic material within its pores to produce water or steam and optionally carbon monoxide, carbon dioxide, and/or oxygenated hydrocarbons. The hydrogen, oxygen, and organic compounds can contact the small pore zeolite in a reactor wherein a portion of the hydrogen and oxygen can contact the catalytic material within the pores of the small pore zeolite and can react to form water or steam. In some examples, a portion of the organic compounds can be too large to fit inside the pores of the small pore zeolite and do not contact the catalytic material. In some examples, at least 80%, 90%, 95%, 99%, or 99.9% of the organic compounds cannot fit inside the pores of the small pore zeolite. In some examples, at least 80%, 90%, 95%, 99%, or 99.9% of the organic compounds do not contact the catalytic metal of the small pore zeolite. In some examples, at least 80%, 90%, or 95% of the organic compounds can have a largest dimension as measured by TEM or molecular modeling and theory of at least 0.43 nm, at least 0.44 nm, at least 0.45 nm, at least 0.46 nm, at least 0.47 nm, at least 0.48 nm, at least 0.49 nm, at least 0.5 nm, at least 0.51 nm, or at least 0.52 nm. some examples, at least 80%, 90%, or 95% of the organic compounds are branched or cyclic hydrocarbons. One method of estimating the amount of organic compounds that contact the catalytic material of the small pore zeolite is to measure the production of carbon monoxide, carbon dioxide, or oxygenated hydrocarbons in the presence of oxygen. In some examples, less than 10 wt %, less than 5 wt %, less than 1 wt %, or less than 0.1 wt % of carbon monoxide can be produced by the selective hydrogen combustion based on the weight of the combined weight of hydrogen, oxygen, and hydrocarbons. In some examples, less than 10 wt %, less than 5 wt %, less than 1 wt %, or less than 0.1 wt % of carbon dioxide can be produced by the selective hydrogen combustion based on the weight of the combined weight of hydrogen, oxygen, and hydrocarbons. In some examples, less than 10 wt %, less than 5 wt %, less than 1 wt %, or less than 0.1 wt % of oxygenated hydrocarbons can be produced by the selective hydrogen combustion based on the weight of the combined weight of hydrogen, oxygen, and hydrocarbons. In some examples, less than 10 wt %, less than 5 wt %, less than 1 wt %, or less than 0.1 wt % of carbon monoxide, carbon dioxide, and/or oxygenated hydrocarbons can be produced by the selective hydrogen combustion based on the weight of the combined weight of hydrogen, oxygen, and hydrocarbons.

In some examples, the hydrogen, oxygen, and organic compounds can contact the small pore zeolite in a reactor at a temperature of from about 20° C. to about 1000° C., about 300° C. to about 800° C., or about 450° C. to about 700° C. In some examples, the hydrogen, oxygen, and organic compounds can contact the small pore zeolite in a reactor at a temperature of less than 350° C., less than 300° C., less than 250° C., or less than 200° C. In some examples, the hydrogen, oxygen, and organic compounds can contact the small pore zeolite in a reactor at a temperature from about 20° C. to about 300° C., about 20° C. to about 250° C., about 50° C. to about 200° C., about 50° C. to about 250° C., or about 50° C. to about 300° C. In some examples, hydrogen, oxygen, and organic compounds can contact the small pore zeolite in a reactor at an absolute pressure from about 0 KPa to about 200 KPa, about 50 KPa to about 150 KPa, or about 75 KPa to about 125 KPa. In some examples, a free oxygen containing gas such as air or pure oxygen can be used as the source of oxygen for the selective hydrogen combustion reaction.

In some examples, the organic compounds can by hydrocarbons. In some examples, the hydrocarbons can be alkanes (e.g., methane, ethane, propane, n-butane, isobutane, n-pentane, isopentane, neopentane), alkenes (e.g., ethene, propene, isobutene, cyclopentene, cyclohexene), aromatics (e.g. benzene, ethylbenzene), naphthenes (e.g. cyclohexane, cyclopentane), alcohols, aldehydes, ketones, esters, ethers, or mixtures thereof. In some examples, the hydrocarbons can be alkanes and alkenes having from 1-30 carbon atoms, 3-30 carbon atoms, 3-15 carbon atoms, 3-10 carbon atoms, 4-30 carbon atoms, 4-15 carbon atoms, or 4-10 carbon atoms. In some examples, the organic compounds can be solid, liquid or gaseous. In some examples, the organic compounds can be gaseous. In some examples, the organic compounds can be dehydrogenatable and dehydrogenated compounds.

In some examples, the small pore zeolite can remove hydrogen as a step in any dehydrogenation reaction. Dehydrogenatable organic compounds can be molecules that contain at least two hydrogen atoms on neighboring atoms bound together by a single or double bond, where one of the hydrogen carrying atoms is carbon and the other one is selected from carbon or a heteroatoms such as oxygen, sulfur, nitrogen and boron. However, molecules containing at least one hydrogen atom can be dehydrogenated too, by removing one hydrogen atom from a single (carbon) atom and coupling two radicals thus formed, as exemplified by the dehydrogenative coupling of methane to ethane. The removal of hydrogen can affect reaction quotient between the forward and the reverse reactions. In some examples, the dehydrogenation reaction can be the preparation of aldehydes or ketones from alcohols, the preparation of alkenes, alkadienes and/or alkynes from alkanes (for example the dehydrogenation of propane to propene, or ethyl benzene to styrene, often catalyzed by chromium oxide on alumina or platinum catalysts), t), the preparation of alkanes by the dehydrogenative coupling of lower alkanes (for example, the dehydrogenative coupling of methane to give ethane and higher alkanes), the preparation of aromatics from hydroaromatics (e.g. the Pd-catalyzed reaction of tetralin to naphthalene), and the preparation of alkadienes from alkenes (such as the dehydrogenation and rearrangement of butene to butadiene and the dehydrogenation of propene to propadiene and propyne). In some examples, the removal of hydrogen can occur as a step in multireactor process. One or more dehydrogenatable organic compounds can be contacted with a dehydrogenation catalyst in a first reactor to produce a first mixture of hydrogen, dehydrogenatable organic compounds, and dehydrogenated organic compounds. The mixture of hydrogen, dehydrogenatable organic compounds, and dehydrogenated organic compounds can be contacted with a synthetic zeolite in a second reactor to produce a second mixture comprising a reduced amount of hydrogen with the production of water or steam. The second mixture can be contacted with a second dehydrogenation catalyst in a third reactor to produce a third mixture comprising an increased amount of the dehydrogenated organic compounds.

Small Pore Zeolite

In some examples, small pore size zeolites, in particular silicates and aluminosilicates, can have a catalytic metal present inside the pores of the zeolite.

In some examples, the small pore size zeolite can be of a framework type AEI, AFT, AFX, CHA, CDO, DDR, EDI, ERI, IHW, ITE, ITW, KFI, MER, MTF, MWF, LEV, LTA, PAU, PWN, RHO, SFW or UFI. In some examples, the small pore size zeolite can be of a framework type of CHA, AEI, AFX, RHO, KFI or LTA. In some examples, the small pore zeolite can be of a framework type CHA or AFX. In some examples, the zeolite framework type can be a framework type that can be synthesized without the use or presence of a structure directing agent. In some examples, the small pore zeolite can be a synthetic zeolite. In some examples, the small pore size zeolite can be of a framework type that requires the presence of a structure directing agent in the synthesis mixture.

In some examples, the small pore size zeolite can be one in which the zeolite framework can contain one or more elements selected from the group consisting of Si, Al, P, As, Ti, Ge, Sn, Fe, B, Ga, Be and Zn. In some examples, the zeolite framework can contain at least one tetravalent element X selected from the group consisting of Si, Ge, Sn and Ti and/or at least one trivalent element Y selected from the group consisting of Al, B, Fe and Ga, optionally at least one pentavalent element Z selected from the group consisting of P and As, and optionally at least one divalent element W selected from the group consisting of Be and Zn. In some examples, the zeolite framework can contain at least Si and/or Al and optionally P. In some examples, the zeolite framework can contain at least one tetravalent element X selected from the group consisting of Si, Ge, Sn and Ti and optionally at least one trivalent element Y selected from the group consisting of Al, B, Fe and Ga. In some examples, the zeolite framework can contain Si and optionally Al and/or B. In some examples, the zeolite framework can contain Si and optionally Al. When the zeolite framework contains a metal, such as Fe, the catalytic metal and transition metal can be different than the metal contained in the framework. The catalytic metal can be an extra-framework metal, that is, the catalytic metal does not form part of the framework of the zeolite, i.e., of the three-dimensional framework of tetrahedra of the zeolite.

In some examples, the small pore size zeolite can be selected from the group consisting of silicates, aluminosilicates, borosilicates, aluminophosphates (ALPOs), and silicoaluminophosphates (SAPOs). In some examples, the small pore size zeolite can be selected from the group consisting of silicates, aluminosilicates and borosilicates. In some examples, the small pore size zeolite can be selected from the group consisting of silicates and aluminosilicates.

The small pore size zeolite can be a crystalline aluminophosphate or silicoaluminophosphate. Aluminophosphate molecular sieves are porous frameworks containing alternating aluminum and phosphorous tetrahedral atoms connected by bridging oxygen atoms. In the case of silicoaluminophosphate molecular sieves, some of the phosphorous, or pairs of aluminum and phosphorous atoms can be substituted with tetrahedral silicon atoms. Those materials can be represented by the formula, on an anhydrous basis:

$$(Si_xAl_yP_z)O_2, \quad mSDA:$$

where m in the number of moles of SDA per mole of $(Si_xAl_yP_z)O_2$ and m has a value in the as-synthesized form of 0.01 to 0.5 or 0.04 to 0.35; x, y, and z represent the mole fraction of Si, Al and P, respectively, as tetrahedral oxides, where x+y+z can be equal to 1, and y and z are greater than or equal to 0.25. In some examples, x can be greater than 0 or greater than 0 to about 0.31. Y can be from 0.25 to 0.5 or 0.4 to 0.5. Z can be from 0.25 to 0.5 or 0.4 to 0.5.

The small pore size zeolite can be a silicate or an aluminosilicate. If the small pore size zeolite is an aluminosilicate, it contains Si and Al and can have a $SiO_2:Al_2O_3$ molar ratio of greater than 4:1, greater than 6:1, greater than 8:1, greater than 10:1, greater than 12:1, greater than 30:1, greater than 100:1, greater than 150:1, from 4:1 to 1000:1, from 4:1 to 100:1, from 6:1 to 1000:1, or from 6:1 to 100:1. If the small pore size zeolite is a silicate, it can have an $Al_2O_3:SiO_2$ molar ratio that is 0 or a $SiO_2:Al_2O_3$ molar ratio that is infinite (i.e. no $Al_2O_3$). While the presence of aluminum within the zeolite framework structure does contribute acidic sites to the catalyst it also is associated with a reduction in thermal stability of the zeolite. Many industrial organic feedstock conversion processes are carried out at temperatures that require the use of zeolite supports having a $SiO_2:Al_2O_3$ molar ratio of greater than 6:1 or even greater than 10:1, such as greater than 12:1 or greater than 30:1 or greater than 100:1 or greater than 150:1.

The small pore size zeolite can have a degree of crystallinity of at least 80%, at least 90%, at least 95% or at least 98%. In some examples, the small pore size zeolite can be an essentially pure crystalline material. The degree of crystallinity can be calculated via x-ray diffraction (XRD) by comparison with a reference material of known 100% crystalline material of the same framework type, the same composition, the same or similar particle size and containing the same amount of metals prepared by an incipient wetness technique. The catalytic metal can be primarily extra-framework metal and can be in the form of metal particles that will tend to scatter x-rays. Therefore, to obtain fully comparable results to calculate the degree of crystallinity, it is important that the reference material contains about the same amount of the same metals as present in the small pore size zeolite. In some examples, the degree of crystallinity can be calculated using the procedure in ASTM D535-197.

In some examples, the synthetic zeolite can have a plurality of pores having an average pore size of less than 0.5 nm, less than 0.45 nm, less than 0.4 nm, less than 0.35 nm, or less than 0.3 nm. In some examples, the synthetic zeolite can have a plurality of pores having an average pore size from 0.3 nm to 0.5 nm, from 0.3 to 0.45 nm, or from 0.3 to 0.4 nm. In some examples, the pore size of the synthetic zeolite can be measured by molecular modeling or X-ray diffraction.

The small pore size zeolite can include at least 0.01 wt % of catalytic metal, based on a weight of the zeolite. The amount of metal can be determined by X-ray fluorescence (XRF) or inductively coupled plasma (ICP) or molecular modeling and can be expressed as wt % of the metal (based on the elemental form of the metal, and not, for example, the oxide form) in the total sample. In some examples, the small pore size zeolite can include at least 0.05 wt %, about 0.01 to about 5 wt %, about 0.05 to about 5 wt %, about 0.1 to about 3 wt %, about 0.5 to about 2.5 wt %, or from about 1 to about 2 wt % of the catalytic metal.

The weight percentage of the catalytic metal in the zeolite can be calculated by carrying out an organic conversion reaction involving a mixed feed having at least one feed compound that is small enough to enter the pores of the zeolite and at least one feed compound that is too large to enter the pores of the zeolite and by comparing the results with an equivalent reaction carried out using a catalyst having an equivalent metal loading in which the metal is not inside the pores, e.g., one in which the metal is supported on amorphous silica. For example, for a hydrogenation catalyst the weight percentage of the catalytic metal that is in the zeolite may be measured by hydrogenation of a mixed feed including a feed compound, such as ethylene, which is small enough to enter the pores of the zeolite and a feed compound, such as propylene, which is too large to enter the pores of the zeolite. In some examples, the smaller compound (e.g., ethylene) and larger compound (e.g., propylene) may be reacted independently rather than as a mixed feed comprising both. This can be advantageous in that it avoids competitive adsorption and diffusion effects that may occur when the smaller and larger compounds are co-fed. In some examples, the conversion of the larger molecule, for example propylene, will be slower than the conversion of the smaller molecule, for example ethylene, relative to the reference catalyst and the degree of difference can be used to calculate the percentage of catalytic metal that is encapsulated in the zeolite. It should be recognized that this method only takes into account the catalytic metal present in the zeolite, i.e., any extra-framework metal that has a catalytic activity is not accounted for. For example, the bulk metal inside any large metal particles present or any catalytic metal covered under dense $SiO_2$ layers will not take part in the reaction and, therefore, will not influence the selectivity and the product mix obtained. For that reason, the words "at least 80% of the catalytic metal is disposed in the pores" and similar expressions should be taken to mean "at least 80% of the catalytically active portion of the catalytic metal is disposed in the pores", it being understood that in many cases the catalytically active portion of the catalytic metal will be all or substantially all of the catalytic metal. In some examples, the percentage of the active catalytic metal that is disposed in the pores in the zeolite (a) can be determined by the following formula:

$$a = \left[ \frac{\frac{PRSiO2}{ERSiO2} - \frac{PRzeolite}{ERzeolite}}{\frac{PRSiO2}{ERSiO2}} \right] * 100$$

where PR is the propylene reaction rate expressed as moles of propylene converted per mole of catalytic metal per second, ER is the ethylene reaction rate expressed as moles of ethylene converted per mole of catalytic metal per second, "PR zeolite" and "ER zeolite" are to be understood as the propylene and ethylene rates of the catalyst to be tested, and "PR $SiO_2$" and "ER $SiO_2$" are to be understood as the propylene and ethylene rates of a catalyst having an equivalent metal loading in which the metal is supported on amorphous silica. Because "a" is the percentage of catalytic metal in the zeolite based on the total amount of catalytic metal whether it is present in the zeolite or on the zeolite surface, "a" is an absolute percentage number regardless of whether the amount of metal in the zeolite or on the zeolite surface is expressed as amounts in weight or mole. Based on the above-referenced formula, an "a" of at least 80% corresponds to an ethylene hydrogenation rate that is at least 5 times greater than that of propylene for metals that hydrogenate both ethylene and propylene at identical rates when supported on $SiO_2$. In some examples, greater than 80%, at least 90%, at least 95%, or at least 98% of the catalytic metal can be inside the pores the zeolite.

In some examples, the catalytic metal can be selected from group consisting of Ru, Rh, Pd, Ag, Os, Ir, Pt, Au, Mo, W, Re, Co, Ni, Zn, Cr, Mn, Ce, Ga, alloys thereof, and mixtures thereof; from the group consisting of Ru, Rh, Pd, Ag, Os, Ir, Pt, Au, Re, alloys thereof, and mixtures thereof; from the group consisting of Pt, Rh, Pd and Au, alloys thereof, and mixtures thereof; or from the group consisting of Pt, Pd and Rh, alloys thereof, and mixtures thereof.

In some examples, the catalytic metal can be present in the form of metal particles, which includes metal clusters as well as site-isolated single metal atoms (the catalytic metal can be present in the particles and/or clusters as elemental metal or as the metal oxide). In some examples, the catalytic metal can be present in the form of particles wherein at least 80%, at least 90%, or at least 95% of the particles by number have a largest dimension of less than 4 nm, less than 3 nm, less than 2 nm or less than 1 nm as measured by TEM. In some examples, at least 80% of the particles by number have a largest dimension in the range of from 0.1 to 3.0 nm, for instance from 0.5 to 1 nm, as measured by TEM. In some examples, after thermal treatment of the small pore size zeolite by calcination in air at 650° C. for two hours and treatment with $H_2$ at 400° C. for two hours, the catalytic metal can be present in the form of particles wherein at least 80% of the particles by number have a largest dimension of less than 4 nm as measured by TEM, in particular at least 80% of the particles by number can have a largest dimension in the range of from 0.1 to 3.0 nm, for instance from 0.5 to 1 nm, as measured by TEM.

The small pore size zeolite can further include one or more metals other than the catalytic metal. In some examples, the small pore size zeolite can include at least 0.01 wt %, from 0.05 to 5 wt %, or from 0.1 to 5 wt % of a transition metal selected from the group consisting of Cu, Fe, Ti, Zr, Nb, Hf, Ta, and combinations thereof. In some examples, this transition metal can be primarily extra-framework metal.

In some examples, a process for the preparation of the small pore zeolite can include: providing a reaction mixture comprising a synthesis mixture capable of forming the small pore size zeolite framework and at least one catalytic metal precursor, wherein the catalytic metal precursor includes metal complexes stabilized by ligands L selected from the group consisting of N-containing ligands, O-containing ligands, S-containing ligands, and P-containing ligands, heating said reaction mixture under crystallization conditions to form crystals of said small pore size zeolite, and recovering said crystals of the small pore size zeolite from the reaction mixture. Without wishing to be bound by theory, it is believed that the ligands L stabilize the metal complex in the synthesis mixture, which is generally highly alkaline, such that it does not become part of the zeolite framework or precipitate from the solution to form large particles that cannot be encapsulated.

The ligand L can be an O-containing ligand, such as an oxalate ion or acetylacetonate ion. Alternatively, the ligand L can be a S-containing ligand, such as a thiol of the structure HS—$(CH_2)_x$-Si—$(OR)_3$, where x=1 to 5 and R=Ci to $C_4$ alkyl, e.g., methyl, ethyl, propyl, or butyl, or x=3 and R=methyl or ethyl, or the S-containing ligand can be an alkyl thiol. In some examples, the ligand L can be a P-containing ligand, such as phosphine, for example, triphenylphosphine. In some examples, the ligand L can be a N-containing ligand, in particular an amine such as $NH_3$, ethylenediamine, diethylenetriamine, triethylenetetramine or tetraethylene pentamine. In some examples, the ligand L can be selected from the group consisting of $NH_3$ and bidentate amines such as ethylene diamine and combinations thereof. The ligand L can be chosen such that the catalytic metal precursor can be stable in the highly alkaline conditions of the synthesis mixture, or in a fluoride media. In some examples, the catalytic metal precursor should be stable against precipitation at the pH of the synthesis mixture under the conditions used to form the small pore zeolite.

In some examples, the catalytic metal precursor can be selected from the group consisting of $[Pt(NH_3)_4]Cl_2$, $[Pt(NH_3)_4](NO_3)_2$, $[Pd(NH_2CH_2CH_2NH_2)_2]Cl_2$, $[Rh(NH_2CH_2CH_2NH_2)_3]Cl_3$, $[Ir(NH_3)_5Cl]Cl_2$, $[Re(NH_2CH_2CH_2NH_2)_2O_2]Cl$, $[Ag(NH_2CH_2CH_2NH_2)]NO_3$, $[Ru(NH_3)_6]Cl_3$, $[Ir(NH_3)_6]Cl_3$, $[Ir(NH_3)_6](NO_3)_3$, $[Ir(NH_3)_5NO_3](NO_3)_2$.

In some examples, the synthesis mixture capable of forming the small pore size synthetic zeolite framework can be a source of a tetravalent element X and/or a source of a trivalent element Y, and optionally a source of a pentavalent element Z, and the molar ratio of the catalytic metal precursor (in terms of metal):$(XO_2+Y_2O_3+Z_2O_5)$ in the synthesis mixture can be in the range of 0.00001 to 0.015, from 0.0001 to 0.010, or from 0.001 to 0.008. In some examples, the synthesis mixture capable of forming the small pore size synthetic zeolite framework can be a source of a tetravalent element X and optionally a source of a trivalent element Y, and the molar ratio of the catalytic metal precursor (in terms of metal):$(XO_2+Y_2O_3)$ in the synthesis mixture can be from 0.00001 to 0.015, from 0.0001 to 0.010, or from 0.001 to 0.008.

In some examples, a process for the preparation of the small pore size synthetic zeolite can include: providing a reaction mixture comprising a synthesis mixture capable of forming the small pore size synthetic zeolite framework, at least one anchoring agent, and at least one catalytic metal precursor, wherein the anchoring agent includes at least one amine and/or thiol group and at least one alkoxysilane group and the catalytic metal precursor includes at least one ligand capable of being exchanged by the at least one amine group and/or thiol group of the anchoring agent, heating said reaction mixture under crystallization conditions to form crystals of said small pore size synthetic zeolite; and recovering said crystals of the small pore size synthetic zeolite from the reaction mixture.

Without wishing to be bound by theory, it is believed that the anchoring agent reacts with the catalytic metal precursor and also with the framework of the zeolite to anchor the catalytic metal precursor in the zeolite as the framework forms. In some examples, the anchoring agent can be a thiol of the structure HS—$(CH_2)_x$—Si—$(OR)_3$, where x can be 1 to 5 and R can be C1 to C4 alkyl, e.g., methyl, ethyl, propyl, or butyl, or x can be 3 and R can be methyl or ethyl. In some examples, the anchoring agent can be an amine of the structure $H_2N$—$(CH_2)_x$—Si—$(OR)_3$, where x can be 1 to 5 and R can be C1 to $C_4$ alkyl, e.g., methyl, ethyl, propyl, or butyl, or x can be 3 and R can be methyl or ethyl. In some examples, the synthesis mixture capable of forming the small pore size synthetic zeolite framework can be a source of a tetravalent element X and/or a source of a trivalent element Y, and optionally a source of a pentavalent element Z, and the molar ratio of anchoring agent:$(XO_2+Y_2O_3+Z_2O_5)$ can be from 0.001 to 0.020 or from 0.002 to 0.015. In some examples, the synthesis mixture capable of forming the small pore size synthetic zeolite framework can be a source of a tetravalent element X and optionally a source of a trivalent element Y, and the molar ratio of anchoring agent:$(XO_2+Y_2O_3)$ can be from 0.001 to 0.020 or from 0.002 to 0.015. In some examples, the molar ratio of catalytic metal precursor (in terms of metal):$(XO_2+Y_2O_3+Z_2O_5)$ or more particularly the molar ratio of catalytic metal precursor (in terms of metal):$(XO_2+Y_2O_3)$ can be from 0.0001 to 0.001, from 0.0002 to less than 0.001, or from 0.0002 to 0.0005. The catalytic metal precursor can be any suitable catalytic metal complex which includes at least one ligand capable of being exchanged by the at least one amine group and/or thiol group of the anchoring agent. In some examples, the catalytic metal precursor can be selected from the group consisting of $H_2PtCl_6$, $H_2PtBr_6$, $Pt(NH_3)_4Cl_2$, $Pt(NH_3)_4(NO_3)_2$, $RuCl_3xH_2O$, $RuBr_3xH_2O$, $RhCl_3xH_2O$, $Rh(NO_3)_3 \cdot xH_2O$, $RhBr_3xH_2O$, $PdCl_2xH_2O$, $Pd(NH_3)_4Cl_2$, $Pd(NH_3)_4B4_2$, $Pd(NH_3)(NO_3)_2$, $AuCl_3$, $HAuBr_4$-$xH_2O$, $HauCl_4$, $HAu(NO_3)_4xH_2O$, $Ag(NO_3)_2$, $ReCl_3$, $Re_2O_7$, $OsCl_3$, $OsO$, $IrBr_3$-$4H_2O$, $IrCl_2$, $IrCl$, $IrCl_3xH_2O$, and $IrBr$, where x can be from 1 to 18, or from 1 to 6.

In an alternative method, preparation of the final metal-containing small pore size synthetic zeolite can include contacting a metal-free small pore zeolite with a metal source, such as a metal salt or metal nanoparticle, followed by calcination in $O_2$ or diluted $O_2$ at elevated temperature (e.g. >400° C.). Without wishing to be bound by any particular theory, in some cases volatile $MO_x$ species with a radius smaller than the pores of a small-pore zeolite can diffuse through the zeolite pores and react with the framework of the zeolite to anchor the catalytic metal species.

In some examples, the synthesis mixture capable of forming the small pore size synthetic zeolite framework can be a source of a tetravalent element X and/or a source of a trivalent element Y, optionally a source of a pentavalent element Z, optionally a source of a divalent element W, optionally a source of an alkali metal M, a source of hydroxide ions and/or a source of halide ions, a source of a structure directing agent (SDA) (in particular a source of an organic structure directing agent (OSDA)), and water. In some examples, the synthesis mixture capable of forming the small pore size synthetic zeolite framework can be a source of a tetravalent element X, optionally a source of a trivalent element Y, optionally a source of an alkali metal M, a source of hydroxide ions and/or a source of halide ions, a source of a structure directing agent (SDA) (in particular a source of an organic structure directing agent (OSDA)), and water.

In some examples, the tetravalent element X can be one or more of Si, Ge, Sn and Ti. Where X=Si, suitable sources of silicon (Si) that can be used to prepare the synthesis mixture include silica; colloidal suspensions of silica, for example that sold by E.I. du Pont de Nemours under the tradename Ludox™; precipitated silica; alkali metal silicates such as potassium silicate and sodium silicate; tetraalkyl orthosilicates; and fumed silicas such as Aerosil and Cabosil.

In some examples, the trivalent element Y can be one or more of B, Al, Fe, and Ga.

In some examples, suitable sources of trivalent element Y that can be used to prepare the synthesis mixture can depend on the element Y that is selected (e.g., boron, aluminum, iron and gallium). In some examples where Y is boron, sources of boron can include boric acid, sodium tetraborate and potassium tetraborate. Sources of boron can be more soluble than sources of aluminum in hydroxide-mediated synthesis systems In some examples, the trivalent element Y can be aluminum, and the aluminum source can includes aluminum sulfate, aluminum nitrate, aluminum hydroxide, hydrated alumina, such as boehmite, gibbsite, and pseudoboehmite, and mixtures thereof. Other aluminum sources include, but are not limited to, other water-soluble aluminum salts, sodium aluminate, aluminum alkoxides, such as aluminum isopropoxide, or aluminum metal, such as aluminum in the form of chips.

Alternatively or in addition to previously mentioned sources of Si and Al, sources containing both Si and Al elements can also be used as sources of Si and Al. Examples of suitable sources containing both Si and Al elements can include amorphous silica-alumina gels, kaolin, metal-kaolin, and zeolites, in particular aluminosilicates such as synthetic faujasite and ultrastable faujasite, for instance USY.

In some examples, suitable sources of pentavalent elements Z depend on the element Z that is selected. In some examples, Z can be phosphorus. Suitable sources of phosphorus can include one or more sources selected from the group consisting of phosphoric acid; organic phosphates, such as triethyl phosphate, tetraethyl-ammonium phosphate; aluminophosphates; and mixtures thereof. In some examples, the synthesis mixture also can contain a source of a divalent element W. In some examples, W can be selected from the group consisting of Be and Zn.

In some examples, the synthesis mixture can also contain a source of halide ions, which can be selected from the group consisting of chloride, bromide, iodide or fluoride, preferably fluoride. The source of halide ions can be any compound capable of releasing halide ions in the molecular sieve synthesis mixture. Non-limiting examples of sources of halide ions include hydrogen fluoride; salts containing one or several halide ions, such as metal halides, where the metal can be sodium, potassium, calcium, magnesium, strontium or barium; ammonium fluoride; or tetraalkylammonium fluorides such as tetramethylammonium fluoride or tetraethylammonium fluoride. If the halide ion is fluoride, a convenient source of halide ion can be HF or $NH_4F$.

In some examples, the synthesis mixture can also contain a source of alkali metal $M^+$. If present, the alkali metal $M^+$ can be selected from the group consisting of sodium, potassium and mixtures of sodium and potassium. The sodium source can be a sodium salt such as NaCl, NaBr, or $NaNO_3$, sodium hydroxide or sodium aluminate. The potassium source can be potassium hydroxide or potassium halide such as KCl or KBr or potassium nitrate.

In some examples, the synthesis mixture can also contain a source of hydroxide ions, for example, an alkali metal hydroxide such as sodium hydroxide or potassium hydroxide. Hydroxide can also be present as a counter ion of the (organic) structure directing agent or by the use of sodium aluminate or potassium aluminate as a source of Y, or by the use of sodium silicate or potassium silicate as the source of X. Sodium or potassium aluminate and silicate can also be used as the source of alkali metal $M^+$.

The synthesis mixture can further include a structure directing agent (SDA), in particular an organic structure directing agent (OSDA). The nature of the SDA (or OSDA) can depend upon the desired framework type. Many such structure directing agents are known to the skilled person. The structure directing agent can be present in any suitable form, for example as a salt of a halide such as a chloride, iodide or bromide, as a hydroxide or as a nitrate. The structure directing agent can be cationic and can be an organic structure directing agent, for example, a nitrogen-containing cation such as a quaternary ammonium cation. For example, the OSDA can be N,N,N-trimethyl-1-adamantammonium hydroxide or iodide (TMAdA) where it is desired to produce a zeolite of framework type CHA or 1, -(hexane-1,6-diyl)bis(1-methylpiperidinium) where it is desired to produce a zeolite of framework type AFX.

The synthesis mixture can have any composition which is suitable for preparing the desired zeolite framework. The following ranges are given as examples of ranges for each pair of components in the synthesis mixture. Conveniently, the molar ratio of $XO_2:Y_2O_3$ in the synthesis mixture may be in the range of from 1 to infinity (i.e. no Y), in particular from 1 to 100 or from 4 to 50. In some examples, the synthesis mixture the molar ratio of $SDA:(XO_2+Y_2O_3+Z_2O_5)$ can be from 0.04 to 0.5 or from 0.08 to 0.3. In some examples, in the synthesis mixture the molar ratio of $H_2O:(XO_2+Y_2O_3)$ can be from 1 to 100 or from 10 to 60. In some examples, in the synthesis mixture the molar ratio of $M^+:(XO_2+Y_2O_3+Z_2O_5)$ can be from 0 to 0.45 or from 0 to 0.20. In some examples, in the synthesis mixture the molar ratio of $OH:(XO_2+Y_2O_3+Z_2O_5)$ can be from 0 to 1.0 or from 0.2 to 0.4. In some examples, in the synthesis mixture the molar ratio of halide:$(XO_2+Y_2O_3+Z_2O_5)$ can be in the range of from 0 to 1 or from 0 to 0.5. In some examples, no Z is present and the molar ratio of $XO_2:Y_2O_3$ in the synthesis mixture can be in the range of from 1 to infinity (i.e. no Y when the zeolite is a silicate), from 1 to 100, or from 4 to 50, e.g., when the zeolite is an aluminosilicate or a borosilicate; the molar ratio of $SDA:(XO_2+Y_2O_3)$ can be from 0.04 to 0.5, from 0.08 to 0.3; the molar ratio of $H_2O:(XO_2+Y_2O_3)$ can be from 1 to 100, or from 10 to 60; the molar ratio of $M^+:(XO_2+Y_2O_3)$ can be from 0 to 0.45 or from 0 to 0.20; the molar ratio of $OH:(XO2+Y_2O_3)$ can be from 0 to 1.0, or from 0.2 to 0.4; and the molar ratio of halide:$(XO_2+Y_2O_3)$ can be from 0 to 1 or from 0 to 0.5. The reaction mixture can have a composition, expressed in terms of mole ratios, as indicated in the following Table:

TABLE 1

| Mole Ratio | | |
| --- | --- | --- |
| $XO_2/Y_2O_3$ | 1 to 100 (or ∞ if no Y) | 4 to 50 (or ∞ if no Y) |
| $SDA/(XO_2+Y_2O_3)$ | 0.04 to 0.5 | 0.08 to 0.3 |
| $H_2O/(XO_2+Y_2O_3)$ | 1 to 100 | 5 to 60 |
| $M^+/(XO_2+Y_2O_3)$ | 0 to 0.45 | 0 to 0.20 |
| $OH^-/(XO_2+Y_2O_3)$ | 0 to 1.0 | 0.2 to 0.4 |
| $Halide^-/(XO_2+Y_2O_3)$ | 0 to 1 | 0 to 0.5 |

The synthesis can be performed with or without added nucleating seeds. If nucleating seeds are added to the synthesis mixture, the seeds can be present in an amount from about 0.01 ppm by weight to about 10,000 ppm by weight, based on the synthesis mixture, such as from about 100 ppm by weight to about 5,000 ppm by weight of the synthesis mixture. The seeds can for instance be of any suitable zeolite, in particular of a zeolite having the same framework as the zeolite to be obtained.

Crystallization can be carried out under either static or stirred conditions in a suitable reactor vessel, such as for example, polypropylene jars or Teflon lined or stainless-steel autoclaves. The crystallization can be typically carried out at a temperature of about 100° C. to about 200° C., such as about 150° C. to about 170° C., for a time sufficient for crystallization to occur at the temperature used, e.g., from about 1 day to about 100 days, in particular from 1 to 50 days, for example from about 2 days to about 40 days. Thereafter, the synthesized crystals can be separated from the mother liquor and recovered.

Since the as-synthesized crystalline zeolite can contain the structure directing agent within its pore structure, the product can be activated before use in such a manner that the organic part of the structure directing agent is at least partially removed from the zeolite. The activation process can be accomplished by calcining, more particularly by heating the zeolite at a temperature of at least about 200° C., at least about 300° C., or at least about 370° C. for at least 1 minute and generally not longer than 20 hours. While subatmospheric pressure can be employed for the thermal treatment, atmospheric pressure can be used for reasons of convenience. The thermal treatment can be performed at a temperature up to about 925° C. For instance, the thermal treatment can be conducted at a temperature of from 400 to 600° C., or from 500 to 550° C., in the presence of an oxygen-containing gas, for example in air.

In some examples, the small pore zeolite can be dehydrated, at least partially. This can be done by heating to a temperature in the range of about 100° C. to about 500° C., such as about 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the zeolite in a vacuum, but a longer time is required to obtain a sufficient amount of dehydration.

Once the zeolite has been synthesized, it can be formulated into a catalyst composition by combination with other materials, such as binders and/or matrix materials that provide additional hardness or catalytic activity to the finished catalyst. These other materials can be inert or catalytically active materials.

In some examples, the small pore zeolite can be incorporated with another material that is resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification. These binder materials are resistant to the temperatures and other conditions, e.g., mechanical attrition, which occur in various hydrocarbon conversion processes. Thus, the small pore zeolite be used in the form of an extrudate with a binder. The extrudate can be formed by extruding the zeolite, optionally in the presence of a binder, and drying and calcining the resulting extrudate.

In some examples, the small pore zeolite can be composited with a porous matrix material such as silica-alumina, silica-magnesia, silica-zirconia, silica-thoria, silica-beryllia, silica-titania as well as ternary compositions such as silicaalumina-thoria, silica-alumina-zirconia, silica-alumina-magnesia and silica-magnesia-zirconia.

The relative proportions of zeolite and inorganic oxide matrix can vary widely, with the content ranging from about 1 to about 90 percent by weight and more usually, particularly when the composite can be prepared in the form of beads, in the range of about 2 to about 80 weight percent of the composite.

EXAMPLES

The foregoing discussion can be further described with reference to the following non-limiting examples.

Example 1: Synthesis of Metal-Free High-Silica CHA Zeolite 800 mg of sodium hydroxide (99 wt %, Sigma-Aldrich) was dissolved in 6.9 g of water. Then, 13.04 g of an aqueous solution of N,N,N-trimethyl-1-adamantammonium hydroxide (TMAdA, 16.2 wt %) was added and maintained under stirring during 15 minutes. At that time, 293 mg of aluminum hydroxide (58 wt %, Sigma-Aldrich) was added, and the resultant mixture kept under stirring at 80° C. for 30 minutes. Finally, 7.5 g of colloidal silica (Ludox AS40, 40 wt %, Aldrich) was introduced in the synthesis mixture, and maintained under stirring at 80° C. for 30 minutes. The final gel composition was SiO2:0.033Al2O3:0.2TMAdA:0.4NaOH:20H2O.

The gel was transferred to an autoclave with a Teflon liner, and heated at 160° C. for 2 days under dynamic conditions. The sample after the hydrothermal crystallization was filtered and washed with abundant distilled water, and finally dried at 100° C.

The solid was characterized by Powder X-ray Diffraction (PXRD), obtaining the characteristic PXRD pattern of the CHA material. Elemental analysis by ICE-AES of the resultant solid indicated a Si/Al of 8.6 (SiO2:Al2O3 molar ratio of 17.2:1).

The Pt-containing CHA was calcined at 550° C. in air in order to remove the organic moieties included inside the microporous material during the crystallization process.

Example 2: Synthesis of Pt Encapsulated in High Silica CHA Zeolite by Post-Synthesis Cation Exchange (0.3% wt Pt/CHA)

6 mg of Pt(NH3)(NO3)2 was dissolved in 10 ml of distilled water. Then, 1 g of the calcined metal-free high-silica CHA zeolite prepared according to the Example 2 was added to the above aqueous solution under agitation (liquid/solid ratio of 10 wt/wt). The mixture was maintained under stirring at room temperature overnight. After this period, the mixture was filtered and washed with abundant water, and the resultant solids calcined at 650° C. in air for 4 hours. Finally, the resultant metal-containing zeolites was treated with H2 at 400° C. for 2 hours.

Example 3: Pt-Containing Amorphous SiC—Comparative 0.01 g of Tetraamine Pt(II) Nitrate in deionized water was impregnated by incipient wetness onto 2 g of silica. The sample was dried at 100° C. and then calcined at 425° C. for 2 hours. The sample was then reduced at 400° C. for 2 hours, to give the Pt/SiO2 sample.

Example 4: Selective Hydrogen Removal

Figure 1:
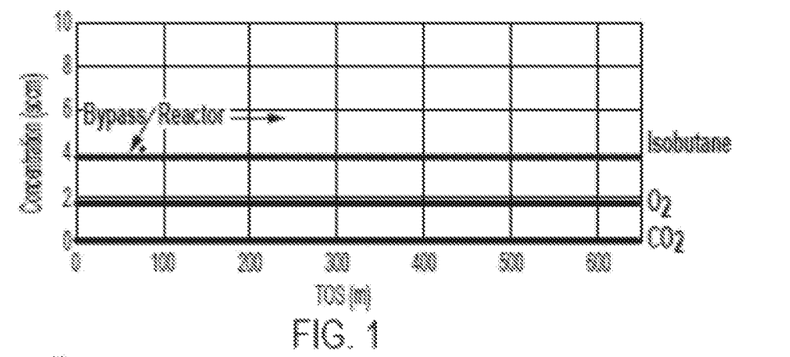
FIG. 1 depicts a graph of isobutane oxidation at 250° C. on a Pt/CHA catalyst.
Figure 2:
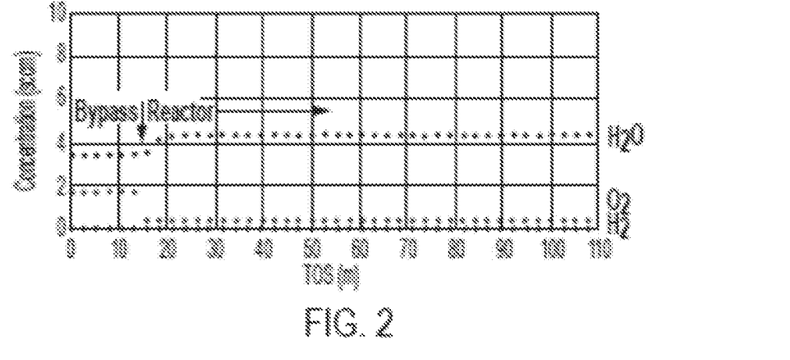
FIG. 2 depicts a graph of hydrogen ($H_2$) oxidation at 250° C. on a Pt/CHA catalyst.
Figure 3:
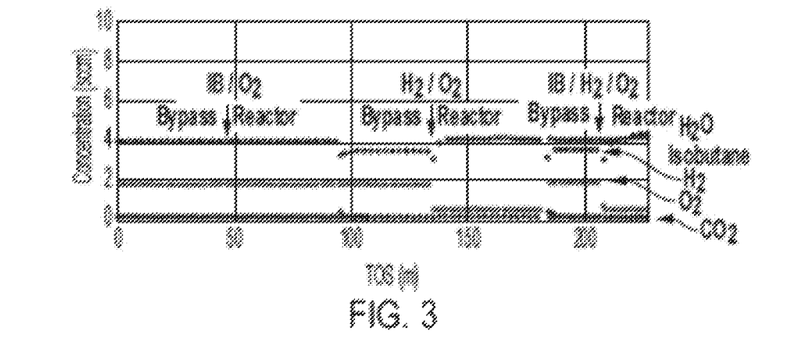
FIG. 3 depicts a graph of competitive oxidation at 250° C. on a Pt/CHA catalyst.
Figure 4:
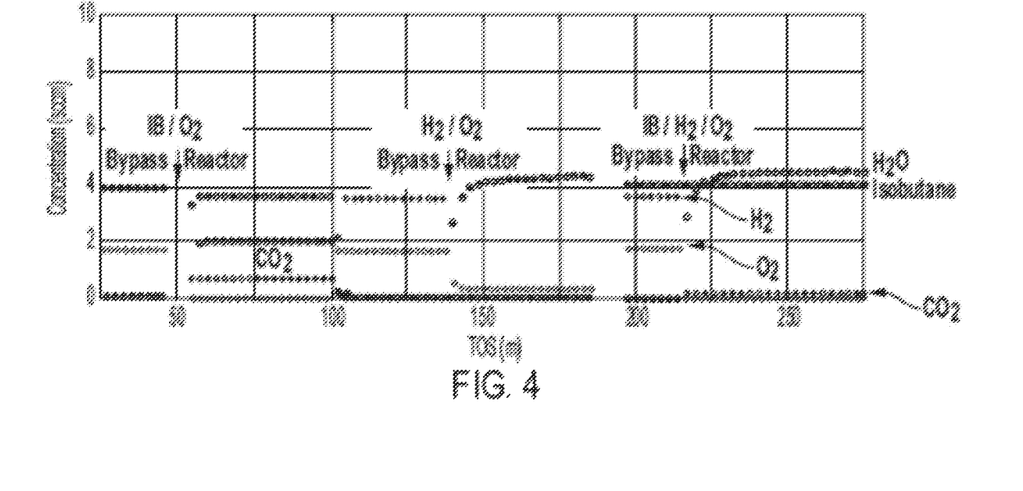
FIG. 4 depicts a graph of competitive oxidation at 250° C. on a Pt/$SiO_2$ catalyst.

A Pt/CHA catalyst including 0.2 wt. % Pt prepared according to Example 2, was tested in comparison with a conventional Pt/SiO2 catalyst prepared according to Example 3 for the selective removal of hydrogen in the presence of isobutane. FIG. 1 shows the results for exposure of the feed containing isobutane to the Pt/CHA catalyst. As shown in FIG. 1, the isobutane does not react with the Pt/CHA catalyst. FIG. 2 shows the results for exposure of the feed containing $H_2$ and $O_2$ to the Pt/CHA catalyst. As shown in FIG. 2, the feed was converted to water. FIG. 3 shows the results for exposure of the feeds containing isobutane, $H_2$ and $O_2$ to the Pt/CHA catalyst. As shown in FIG. 3, the isobutane does not react with the Pt/CHA catalyst and the $H_2$ and $O_2$ react to form water. FIG. 4 shows the results for exposure of the feed containing isobutane, $H_2$ and $O_2$ to the Pt/SiO2 catalyst. As shown in FIG. 4, both isobutane and $H_2$ react with the Pt/SiO2 catalyst.

Embodiment 1. A process for the removal of hydrogen from a mixture, comprising: contacting a mixture comprising hydrogen, oxygen, and one or more organic compounds with a synthetic zeolite to produce water or steam, wherein the synthetic zeolite comprises, Si and Al and has a $SiO_2$:$Al_2O_3$ molar ratio of greater than 4:1, an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI, a degree of crystallinity of at least 80% as measured by ASTM D535-197, and at least 0.01 wt % of at least one catalytic metal, based on a weight of the synthetic zeolite, wherein the at least one catalytic metal comprises Ru, Rh, Pd, Ag, Os, Ir, Pt, Au, Mo, W, Re, Co, Ni, Zn, Cr, Mn, Ce, Ga, alloys thereof, or mixtures thereof, wherein at least 95% of the catalytic metal is disposed within a plurality of pores of the synthetic zeolite.

Embodiment 2. The process of Embodiment 1, wherein the plurality of pores have an average pore size of less than 0.5 nm as measured by molecular modeling.

Embodiment 3. The process of Embodiment 1 or Embodiment 2, wherein the synthetic zeolite has a framework comprising Si, Al, P, As, Ti, Ge, Sn, Fe, B, Ga, Be, Zn, alloys thereof, or mixtures thereof.

Embodiment 4. The process of any of Embodiments 1 to 3, wherein the synthetic zeolite comprises a silicate, an aluminosilicate, or a borosilicate.

Embodiment 5. The process of any of Embodiments 1 to 4, wherein the synthetic zeolite has a $SiO_2$:$Al_2O_3$ molar ratio of greater than 6:1.

Embodiment 6. The process of any of Embodiments 1 to 5, wherein the synthetic zeolite further comprises at least 0.01 wt % of a transition metal comprising Cu, Fe, Ti, Zr, Nb, Hf, Ta, alloys thereof, or mixtures thereof, wherein the transition metal is an extra-framework metal.

Embodiment 7. The process of any of Embodiments 1 to 6, wherein at least 90% of the catalytic metal is disposed in the plurality of pores of the synthetic zeolite.

Embodiment 8. The process of any of Embodiments 1 to 7, wherein the at least one catalytic metal comprises Ru, Rh, Pd, Ag, Os, Ir, Pt, Au, Re, alloys thereof, or mixtures thereof.

Embodiment 9. The process of any of Embodiments 1 to 8, wherein at least one catalytic metal is in a particulate form and at least 80% of the particles by number have a largest dimension of less than 2 nm as measured by TEM.

Embodiment 10. The process of any of Embodiments 1 to 9, wherein the at least one catalytic metal comprises Pt, Rh, Pd, Au, alloys thereof, or mixtures thereof and wherein the synthetic zeolite is an 8-membered ring zeolite having a framework type of CHA, AEI, AFX, RHO, KFI or LTA and the synthetic zeolite is a silicate or an aluminosilicate, wherein the aluminosilicate has an $SiO_2:Al_2O_3$ molar ratio of greater than 6:1.

Embodiment 11. The process of any of Embodiments 1 to 10, wherein the synthetic zeolite comprises a structure directing agent (SDA).

Embodiment 12. The process of any of Embodiments 1 to 11, wherein the synthetic zeolite is calcined.

Embodiment 13. The process of any of Embodiments 1 to 12, wherein at least 80% of the one or more organic compounds are branched or cyclic hydrocarbons.

Embodiment 14. The process of any of Embodiments 1 to 13, wherein at least 90% of the one or more organic compounds are branched or cyclic hydrocarbons.

Embodiment 15. The process of any of Embodiments 1 to 14, wherein the one or more organic compounds comprise a dehydrogenatable organic compound and the process further comprises the step of dehydrogenating at least a portion of the dehydrogenatable organic compound to produce a dehydrogenated organic compound and hydrogen.

Embodiment 16. The process of any of Embodiments 1 to 15, wherein the one or more organic compounds comprises a mixture of one or more alkanes having from 4 to 10 carbon atoms and one or more alkenes having from 4 to 10 carbon atoms.

Embodiment 17. The process of any of Embodiments 1 to 16, further comprising recovering at least a portion of the one or more organic compounds.

Embodiment 18. The process of any of Embodiments 1 to 17, wherein the synthetic zeolite has a $SiO_2:Al_2O_3$ molar ratio from 4:1 to 1000:1.

Embodiment 19. A process for the removal of hydrogen from a mixture, comprising: contacting a mixture comprising hydrogen, oxygen, and one or more organic compounds with a synthetic zeolite, wherein at least 80% of the one or more organic compounds are branched or cyclic hydrocarbons and wherein the synthetic zeolite comprises, a degree of crystallinity of at least 80% as measured by ASTM D535-197, an 8-membered ring zeolite having a framework type of CHA; and at least 0.01 wt % of at least one catalytic metal, based on a weight of the synthetic zeolite, wherein the at least one catalytic metal comprises Ru, Rh, Pd, Ag, Os, Ir, Pt, Au, Mo, W, Re, Co, Ni, Zn, Cr, Mn, Ce, Ga, alloys thereof, or mixtures thereof, wherein at least 95% of the catalytic metal is disposed within a plurality of pores of the synthetic zeolite.

Embodiment 20. The process of Embodiment 19, wherein the synthetic zeolite is a silicate, an aluminosilicate, or a borosilicate.

Embodiment 21. The process of Embodiment 19 or Embodiment 20, wherein the synthetic zeolite comprises Si and Al and has a $SiO_2:Al_2O_3$ molar ratio of greater than 6:1.

Embodiment 22. The process of any of Embodiments 19 to 21, wherein the synthetic zeolite further comprises at least 0.01 wt % of a transition metal selected from the group consisting of Cu, Fe, Ti, Zr, Nb, Hf, Ta and combinations thereof, wherein the transition metal is an extra-framework metal.

Embodiment 23. The process of any of Embodiments 19 to 22, wherein the at least one catalytic metal is in a particulate form and at least 80% of the particles by number have a largest dimension of less than 2 nm as measured by TEM.

Embodiment 24. The process of any of Embodiments 19 to 23, wherein the at least one catalytic metal comprises Ru, Rh, Pd, Ag, Os, Ir, Pt, Au, Re, alloys thereof, or mixtures thereof.

Embodiment 25. The process of any of Embodiments 19 to 24, wherein the at least one catalytic metal is in a particulate form and at least 95% of the particles by number have a largest dimension of less than 2 nm as measured by TEM.

Embodiment 26. The process of any of Embodiments 19 to 25, wherein the at least one catalytic metal comprises Pt, Rh, Pd, Au, alloys thereof, or mixtures thereof and wherein the synthetic zeolite is a silicate or an aluminosilicate, wherein the aluminosilicate has an $SiO_2:Al_2O_3$ molar ratio of greater than 6:1.

Embodiment 27. The process of any of Embodiments 19 to 26, wherein the synthetic zeolite comprises a structure directing agent (SDA).

Embodiment 28. The process of any of Embodiments 19 to 27, wherein the synthetic zeolite is calcined.

Embodiment 29. The process of any of Embodiments 19 to 28, wherein at least 90% of the one or more organic compounds are branched or cyclic hydrocarbons.

Embodiment 30. The process of any of Embodiments 19 to 29, wherein the one or more organic compounds comprise a dehydrogenatable organic compound and the process further comprises the step of dehydrogenating at least a portion of the dehydrogenatable organic compound to produce a dehydrogenated organic compound and the hydrogen.

Embodiment 31. The process of any of Embodiments 19 to 30, wherein the one or more organic compounds comprises a mixture of one or more alkanes having from 4 to 10 carbon atoms and one or more alkenes having from 4 to 10 carbon atoms.

Embodiment 32. The process of any of Embodiments 19 to 31, further comprising the step of recovering at least a portion of the one or more organic compounds.

Embodiment 33. The process of any of Embodiments 19 to 32, wherein the hydrogen reacts with oxygen in the presence of the catalytic metal to produce water.

Embodiment 34. A process for the removal of hydrogen from a mixture, comprising: contacting one or more dehydrogenatable organic compounds with a first dehydrogenation catalyst in a first reactor to produce a first mixture of hydrogen, dehydrogenatable organic compounds, and dehydrogenated organic compounds, contacting the mixture of hydrogen, dehydrogenatable organic compounds, and dehydrogenated organic compounds with a synthetic zeolite in a second reactor to produce a second mixture comprising a reduced amount of hydrogen, wherein the synthetic zeolite comprises, Si and Al and has a SiO2:Al2O3 molar ratio of greater than 4:1, a degree of crystallinity of at least 80% as measured by ASTM D535-197, an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI; and at least 0.01 wt % of at least one catalytic metal, based on a weight of the synthetic zeolite, wherein the at least one catalytic metal comprises Ru, Rh, Pd, Ag, Os, Ir, Pt, Au, Mo, W, Re, Co, Ni, Zn, Cr, Mn, Ce, Ga, alloys thereof, or mixtures thereof, wherein at least 95% of the catalytic metal is disposed within a plurality of pores of the synthetic zeolite; and contacting the second mixture with a second dehydrogenation catalyst in a third reactor to produce a third mixture comprising an increased amount of the dehydrogenated organic compounds.

Embodiment 35. The process of Embodiment 34, wherein the synthetic zeolite is a silicate, an aluminosilicate, or a borosilicate.

Embodiment 36. The process of Embodiment 34 or Embodiment 35, wherein the synthetic zeolite has a $SiO_2$:$Al_2O_3$ molar ratio of greater than 6:1.

Embodiment 37. The process of any of Embodiments 34 to 36, wherein the synthetic zeolite further comprises at least 0.01 wt % of a transition metal selected from the group consisting of Cu, Fe, Ti, Zr, Nb, Hf, Ta and combinations thereof, wherein the transition metal is an extra-framework metal.

Embodiment 38. The process of any of Embodiments 34 to 37, wherein the at least one catalytic metal is in a particulate form and at least 80% of the particles by number have a largest dimension of less than 2 nm as measured by TEM.

Embodiment 39. The process of any of Embodiments 34 to 38, wherein the at least one catalytic metal comprises Ru, Rh, Pd, Ag, Os, Ir, Pt, Au, Re, alloys thereof, or mixtures thereof.

Embodiment 40. The process of any of Embodiments 34 to 39, wherein the at least one catalytic metal is in a particulate form and at least 95% of the particles by number have a largest dimension of less than 2 nm as measured by TEM.

Embodiment 41. The process of any of Embodiments 34 to 40, wherein the at least one catalytic metal comprises Pt, Rh, Pd, Au, alloys thereof, or mixtures thereof and wherein the synthetic zeolite is a silicate or an aluminosilicate, wherein the aluminosilicate has an $SiO_2$:$Al_2O_3$ molar ratio of greater than 6:1.

Embodiment 42. The process of any of Embodiments 34 to 41, wherein the synthetic zeolite comprises a structure directing agent (SDA).

Embodiment 43. The process of any of Embodiments 34 to 42, wherein the synthetic zeolite is calcined.

Embodiment 44. The process of any of Embodiments 34 to 43, wherein at least 90% of the one or more organic compounds are branched or cyclic hydrocarbons.

Embodiment 45. The process of any of Embodiments 34 to 44, wherein the one or more organic compounds comprise a dehydrogenatable organic compound and the process further comprises the step of dehydrogenating at least a portion of the dehydrogenatable organic compound to produce a dehydrogenated organic compound and the hydrogen.

Embodiment 46. The process of any of Embodiments 34 to 45, wherein the one or more organic compounds comprises a mixture of one or more alkanes having from 4 to 10 carbon atoms and one or more alkenes having from 4 to 10 carbon atoms.

Embodiment 47. The process of any of Embodiments 4 to 46, further comprising the step of recovering at least a portion of the one or more organic compounds.

Embodiment 48. The process of any of Embodiments 34 to 47, wherein the hydrogen reacts with oxygen in the presence of the catalytic metal to produce water.

Embodiment 49. A process for the removal of hydrogen from a mixture, comprising: contacting a mixture comprising hydrogen, oxygen, and one or more organic compounds with a synthetic zeolite at a temperature of less than 250° C. to produce water or steam, wherein the synthetic zeolite comprises, an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI, a degree of crystallinity of at least 80% as measured by ASTM D535-197, and at least 0.01 wt % of at least one catalytic metal, based on a weight of the synthetic zeolite, wherein the at least one catalytic metal comprises Ru, Rh, Pd, Ag, Os, Ir, Pt, Au, Mo, W, Re, Co, Ni, Zn, Cr, Mn, Ce, Ga, alloys thereof, or mixtures thereof, and wherein at least 95% of the catalytic metal is disposed within a plurality of pores of the synthetic zeolite.

Embodiment 50. The process of Embodiment 49, wherein the synthetic zeolite is a silicate, an aluminosilicate, or a borosilicate.

Embodiment 51. The process of Embodiment 49 or Embodiment 50, wherein the synthetic zeolite comprises Si and Al and has a $SiO_2$:$Al_2O_3$ molar ratio of greater than 6:1.

Embodiment 52. The process of any of Embodiments 49 to 51, wherein the synthetic zeolite further comprises at least 0.01 wt % of a transition metal selected from the group consisting of Cu, Fe, Ti, Zr, Nb, Hf, Ta and combinations thereof, wherein the transition metal is an extra-framework metal.

Embodiment 53. The process of any of Embodiments 49 to 52, wherein the at least one catalytic metal is in a particulate form and at least 80% of the particles by number have a largest dimension of less than 4 nm as measured by TEM.

Embodiment 54. The process of any of Embodiments 49 to 53, wherein the at least one catalytic metal comprises Ru, Rh, Pd, Ag, Os, Ir, Pt, Au, Re, alloys thereof, or mixtures thereof.

Embodiment 55. The process of any of Embodiments 49 to 54, wherein the at least one catalytic metal is in a particulate form and at least 95% of the particles by number have a largest dimension of less than 2 nm as measured by TEM.

Embodiment 56. The process of any of Embodiments 49 to 55, wherein the at least one catalytic metal comprises Pt, Rh, Pd, Au, alloys thereof, or mixtures thereof and wherein the synthetic zeolite is a silicate or an aluminosilicate, wherein the aluminosilicate has an $SiO_2$:$Al_2O_3$ molar ratio of greater than 6:1.

Embodiment 57. The process of any of Embodiments 49 to 56, wherein the synthetic zeolite comprises a structure directing agent (SDA).

Embodiment 58. The process of any of Embodiments 49 to 57, wherein the synthetic zeolite is calcined.

Embodiment 59. The process of any of Embodiments 49 to 58, wherein at least 90% of the one or more organic compounds are branched or cyclic hydrocarbons.

Embodiment 60. The process of any of Embodiments 49 to 59, wherein the one or more organic compounds comprise a dehydrogenatable organic compound and the process further comprises the step of dehydrogenating at least a portion of the dehydrogenatable organic compound to produce a dehydrogenated organic compound and the hydrogen.

Embodiment 61. The process of any of Embodiments 49 to 60, wherein the one or more organic compounds comprises a mixture of one or more alkanes having from 4 to 10 carbon atoms and one or more alkenes having from 4 to 10 carbon atoms.

Embodiment 62. The process of any of Embodiments 49 to 61, further comprising the step of recovering at least a portion of the one or more organic compounds.

Embodiment 63. The process of any of Embodiments 49 to 62, wherein the hydrogen reacts with oxygen in the presence of the catalytic metal to produce water.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

The invention claimed is:

1. A process for the removal of hydrogen from a mixture, comprising:
   contacting a mixture comprising hydrogen, oxygen, and one or more organic compounds with a synthetic zeolite to produce water or steam, wherein the synthetic zeolite comprises,
   Si and Al and has a $SiO_2:Al_2O_3$ molar ratio of greater than 4:1,
   an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI,
   a degree of crystallinity of at least 80% as measured by ASTM D535-197, and
   at least 0.01 wt % of at least one catalytic metal, based on a weight of the synthetic zeolite, wherein the at least one catalytic metal comprises Ru, Rh, Pd, Ag, Os, Ir, Pt, Au, Mo, W, Re, Co, Ni, Zn, Cr, Mn, Ce, Ga, alloys thereof, or mixtures thereof, wherein at least 95% of the catalytic metal is disposed within a plurality of pores of the synthetic zeolite.

2. The process of claim 1, wherein the plurality of pores have an average pore size of less than 0.5 nm as measured by molecular modeling.

3. The process of claim 1, wherein the synthetic zeolite has a framework comprising Si, Al, P, As, Ti, Ge, Sn, Fe, B, Ga, Be, Zn, alloys thereof, or mixtures thereof.

4. The process of any claim 1, wherein the synthetic zeolite comprises a silicate, an aluminosilicate, or a borosilicate.

5. The process of claim 1, wherein the synthetic zeolite has a $SiO_2:Al_2O_3$ molar ratio of greater than 6:1.

6. The process of claim 1, wherein the synthetic zeolite further comprises at least 0.01 wt % of a transition metal comprising Cu, Fe, Ti, Zr, Nb, Hf, Ta, alloys thereof, or mixtures thereof, wherein the transition metal is an extra-framework metal.

7. The process of claim 1, wherein at least 90% of the catalytic metal is disposed in the plurality of pores of the synthetic zeolite.

8. The process of claim 1, wherein the at least one catalytic metal comprises Ru, Rh, Pd, Ag, Os, Ir, Pt, Au, Re, alloys thereof, or mixtures thereof.

9. The process of claim 1, wherein at least one catalytic metal is in a particulate form and at least 80% of the particles by number have a largest dimension of less than 2 nm as measured by TEM.

10. The process of claim 1, wherein the at least one catalytic metal comprises Pt, Rh, Pd, Au, alloys thereof, or mixtures thereof and wherein the synthetic zeolite is an 8-membered ring zeolite having a framework type of CHA, AEI, AFX, RHO, KFI or LTA and the synthetic zeolite is a silicate or an aluminosilicate, wherein the aluminosilicate has an $SiO_2:Al_2O_3$ molar ratio of greater than 6:1.

11. The process of claim 1, wherein the one or more organic compounds comprise a dehydrogenatable organic compound and the process further comprises the step of dehydrogenating at least a portion of the dehydrogenatable organic compound to produce a dehydrogenated organic compound and hydrogen.

12. The process of claim 1, wherein the one or more organic compounds comprises a mixture of one or more alkanes having from 4 to 10 carbon atoms and one or more alkenes having from 4 to 10 carbon atoms.

13. A process for the removal of hydrogen from a mixture, comprising:
   contacting a mixture comprising hydrogen, oxygen, and one or more organic compounds with a synthetic zeolite, wherein at least 80% of the one or more organic compounds are branched or cyclic hydrocarbons and wherein the synthetic zeolite comprises,
   a degree of crystallinity of at least 80% as measured by ASTM D535-197,
   an 8-membered ring zeolite having a framework type of CHA; and
   at least 0.01 wt % of at least one catalytic metal, based on a weight of the synthetic zeolite, wherein the at least one catalytic metal comprises Ru, Rh, Pd, Ag, Os, Ir, Pt, Au, Mo, W, Re, Co, Ni, Zn, Cr, Mn, Ce, Ga, alloys thereof, or mixtures thereof, wherein at least 95% of the catalytic metal is disposed within a plurality of pores of the synthetic zeolite.

14. The process of claim 13, wherein the at least one catalytic metal is in a particulate form and at least 80% of the particles by number have a largest dimension of less than 4 nm as measured by TEM.

15. The process of claim 13, wherein the at least one catalytic metal is in a particulate form and at least 95% of the particles by number have a largest dimension of less than 2 nm as measured by TEM.

16. The process of claim 13, wherein the at least one catalytic metal comprises Pt, Rh, Pd, Au, alloys thereof, or mixtures thereof and wherein the synthetic zeolite is a silicate or an aluminosilicate, wherein the aluminosilicate has an $SiO_2:Al_2O_3$ molar ratio of greater than 6:1.

17. The process of claim 13, wherein the synthetic zeolite comprises a structure directing agent (SDA).

18. The process of claim 13, wherein the one or more organic compounds comprise a dehydrogenatable organic compound and the process further comprises the step of dehydrogenating at least a portion of the dehydrogenatable organic compound to produce a dehydrogenated organic compound and the hydrogen.

19. The process of claim 13, wherein the one or more organic compounds comprises a mixture of one or more alkanes having from 4 to 10 carbon atoms and one or more alkenes having from 4 to 10 carbon atoms.

20. The process of claim 13, further comprising the step of recovering at least a portion of the one or more organic compounds.

21. The process of claim 13, wherein the hydrogen reacts with oxygen in the presence of the catalytic metal to produce water.

22. A process for the removal of hydrogen from a mixture, comprising:
- contacting one or more dehydrogenatable organic compounds with a first dehydrogenation catalyst in a first reactor to produce a first mixture of hydrogen, dehydrogenatable organic compounds, and dehydrogenated organic compounds,
- contacting the mixture of hydrogen, dehydrogenatable organic compounds, and dehydrogenated organic compounds with a synthetic zeolite in a second reactor to produce a second mixture comprising a reduced amount of hydrogen, wherein the synthetic zeolite comprises,
  - Si and Al and has a $SiO_2:Al_2O_3$ molar ratio of greater than 4:1,
  - a degree of crystallinity of at least 80% as measured by ASTM D535-197,
  - an 8-membered ring zeolite having a framework type of AEI, AFT, AFX, CHA, CDO, DDR, EDI, ERI, IHW, ITE, ITW, KFI, MER, MTF, MWF, LEV, LTA, PAU, PWN, RHO, SFW or UFI; and
  - at least 0.01 wt % of at least one catalytic metal, based on a weight of the synthetic zeolite, wherein the at least one catalytic metal comprises Ru, Rh, Pd, Ag, Os, Ir, Pt, Au, Mo, W, Re, Co, Ni, Zn, Cr, Mn, Ce, Ga, alloys thereof, or mixtures thereof, wherein at least 95% of the catalytic metal is disposed within a plurality of pores of the synthetic zeolite; and
- contacting the second mixture with a second dehydrogenation catalyst in a third reactor to produce a third mixture comprising an increased amount of the dehydrogenated organic compounds.

23. The process of claim 22, wherein the at least one catalytic metal is in a particulate form and at least 95% of the particles by number have a largest dimension of less than 2 nm as measured by TEM.

24. The process of claim 22, wherein the at least one catalytic metal comprises Pt, Rh, Pd, Au, alloys thereof, or mixtures thereof and wherein the synthetic zeolite is a silicate or an aluminosilicate, wherein the aluminosilicate has an $SiO_2:Al_2O_3$ molar ratio of greater than 6:1.

25. The process of claim 22, wherein the synthetic zeolite comprises a structure directing agent (SDA).

* * * * *